(12) United States Patent
Hurwitz et al.

(10) Patent No.: US 7,396,976 B2
(45) Date of Patent: Jul. 8, 2008

(54) EASY-TO-PEEL SECURELY ATTACHING BANDAGE

(75) Inventors: Marni Markell Hurwitz, Far Hills, NJ (US); Dave Narasimhan, Flemington, NJ (US); Ernest D. Buff, Far Hills, NJ (US)

(73) Assignee: I DID IT, Inc., Far Hills, NJ (US)

( * ) Notice: Subject to any disclaimer, the term of this patent is extended or adjusted under 35 U.S.C. 154(b) by 0 days.

(21) Appl. No.: 11/408,502

(22) Filed: Apr. 21, 2006

(65) Prior Publication Data

US 2007/0249981 A1   Oct. 25, 2007

(51) Int. Cl.
*A61F 13/00* (2006.01)

(52) U.S. Cl. .............................. 602/58; 602/41; 602/42; 602/54

(58) Field of Classification Search ......... 604/304–308; 602/41–43, 48, 52, 54–56, 57; 424/443–449
See application file for complete search history.

(56) References Cited

U.S. PATENT DOCUMENTS

| | | | |
|---|---|---|---|
| 4,140,115 A | 2/1979 | Schonfeld | 602/54 |
| 4,693,776 A | 9/1987 | Krampe et al. | 156/327 |
| 4,732,808 A | 3/1988 | Krampe et al. | 428/355 CN |
| 5,412,035 A | 5/1995 | Schmitt et al. | 525/93 |
| 5,653,224 A * | 8/1997 | Johnson | 128/200.24 |
| 5,947,917 A | 9/1999 | Carte et al. | 602/52 |
| 6,077,589 A | 6/2000 | De Carvalho | 428/131 |
| 6,368,687 B1 | 4/2002 | Joseph et al. | 428/40.1 |
| 6,566,577 B1 | 5/2003 | Addison et al. | 602/56 |
| 6,743,964 B2 | 6/2004 | Yoshida et al. | 602/43 |
| 6,747,183 B2 | 6/2004 | Siegwart et al. | 602/58 |
| 6,942,683 B2 | 9/2005 | Dunshee | 606/214 |
| 6,946,177 B2 | 9/2005 | Abe et al. | 428/40.1 |
| 2005/0066965 A1 * | 3/2005 | Cronk et al. | 128/200.24 |

* cited by examiner

*Primary Examiner*—Kim M Lewis
(74) *Attorney, Agent, or Firm*—Ernest D. Buff & Associates, LLC; Ernest D. Buff; Dave Narasimhan

(57) ABSTRACT

A bandage remains securely attached to the skin of a wearer during extended exposure to arid, humid or wet conditions. The bandage is readily removed from the attached condition upon application of pressure to its exterior surface. Adhesive portions of the contain pockets or microcapsules filled with an adhesive-inactivating ingredient. The pockets are formed in the backing layer. Microcapsules, if present, are incorporated in the adhesive. The adhesive inactivating ingredient comprises oil from vegetable source, mineral source or fatty acids. The wearer ruptures the pockets or microcapsules by applying pressure to the bandage above the adhesive portions. The adhesive-inactivating ingredient is thereby released at the skin-adhesive interface, permitting an easy, pain-free removal of the bandage.

5 Claims, 3 Drawing Sheets

EASY-TO-PEEL SECURELY ATTACHING BANDAGE

BACKGROUND OF THE INVENTION

1. Field of the Invention

The present invention relates to bandages; and, more particularly to releasable bandages, such as wound dressings, gauze retainers or splints that remain securely attached during use, but can be painlessly released upon demand.

2. Description of the Prior Art

Bandages are well known in the art and are used for various medical applications and sports protection. Sterile bandages marketed under well-recognized trade names, such as 'Band-Aid', 'Cural' and the like, that provide secure attachment of the bandage's adhesive portion to bare skin adjacent to a wound. A sterile wound-covering pad contacts the wound. More recently, adhesives have been developed for bandages that do not peel off even when the bandage is wetted by sweat or swimming activity. The corners of the bandages are oftentimes shaped to prevent easy release of the bandage. All these developments prevent easy removal of the bandage, especially when the area of the skin is covered with hair. Bandage removal is typically so painful that most patients and doctors remove the bandage by pulling sharply, as fast as possible, to minimize the duration of pain. No solution is presently available that allows easy, pain-free or reduced-pain removal of a bandage. The pain problem becomes more severe as the size of the bandage increases, as is the case for splint restrainers or gauzes.

Several patents detail construction of bandages and selection of adhesives, which improve skin adhesion. Some patents address the shape of the bandage so that the edges do not readily peel off. Some patents provide a covering that prevents the wound-contacting portion of the dressing from sticking to the wound, thereby reducing pain of bandage removal. None of these patents addresses the problem of pain associated with removal of the adhesive tape that retains the bandage against the skin.

Several patents address use of release layers normally coated on the side of a bandage opposed to the adhesive coated surface, enabling the peeling of a wound adhesive tape. This release layer is applied to the backside that is opposed to the adhesive side of the polymeric tape and has nothing to do with the release of the tape from the skin. These tape release compositions are not discussed. In fact, the presence of this release layer on the skin is not useful since the tape will no longer adhere to the skin.

U.S. Pat. No. 4,140,115 to Schonfeld discloses pressure sensitive adhesive compositions for coating articles to be attached to skin. Skin damage, i.e., the stripping of tissue cells from the stratum corneum, caused by removal of a backing material which has been held in adherent contact with a skin surface by means of a pressure sensitive adhesive composition coated on the backing material, is markedly reduced by incorporation of about 4 to 20% by weight of an unreacted polyol uniformly dispersed in the water-insoluble pressure sensitive adhesive mass. Suitable polyols include polyethylene glycol and polypropylene sorbitol monolaurate. The unreacted polyol is always present in the adhesive reducing the tackiness of the adhesive and easy release of the adhesive tape is achieved at the expense of the adhesive properties.

U.S. Pat. Nos. 4,693,776 and 4,732,808 to Krampe et al. disclose macromer reinforced pressure sensitive skin adhesive sheet material. A skin adhesive coated sheet material is provided which is coated with a polymer that exhibits an enhanced level of initial adhesion when applied to skin but resists objectionable adhesion build up over time. The skin adhesives are comprised of a macromer reinforced acrylate copolymer, which has a creep compliance value at least about $1.2 \times 10^{-5}$ cm$^2$/dyne. A stable chemical complex of iodine, iodide and a pressure-sensitive adhesive is also provided wherein the adhesive has a creep compliance value of at least about $1.0 \times 10^{-5}$ cm$^2$/dyne measured when the adhesive composition is substantially free of iodine. The adhesive contains a monomeric acrylate or methacrylate ester of a non-tertiary alcohol, at least one ethylenically unsaturated compound copolymerizable with monomeric acrylate or methacrylate ester and a macromer. The addition of these macromer is always present in the adhesive, which degrades as a function. Easy peel of the adhesive layer does not occur until this degradation has occurred and the bandage cannot be removed without pain at any time selected by the user.

U.S. Pat. No. 5,412,035 to Schmitt et al. discloses pressure-sensitive adhesives. Pressure-sensitive adhesive compositions containing a crystalline polymeric additive having a molecular weight of less than 25,000 and a melting point greater than 23 degree C., preferably 30 to 60 degree C., coated on a flexible backing. The presence of the additive causes the pressure sensitive adhesive to lose adhesive strength when heated to the melting point of the additive. The base resin of the pressure sensitive adhesive is a polyacrylate or a styrene/butadiene copolymer. The additive, which is a side chain crystallizable polymer, is present in an amount ranging from 1 to 35%. Heat has to be applied to release this bandage. Application of heat to a wound is extremely painful and may, in the worst case, retard the healing process of the wound.

U.S. Pat. No. 5,947,917 to Carte et al. discloses an adhesive bandage or tape. A water resistant, flexible, dermal adhesive product for conformable topical application to human skin, the dermal adhesive product comprising a backing sheet having an adhesive for removably adhering the sheet to the skin, wherein the adhesive is a highly crosslinked pressure sensitive adhesive composition comprising the polymerization reaction product of about 75% to about 95% of a mixture of at least two alkyl acrylate or methacrylate esters, about 1% to about 10% ethylenically unsaturated carboxylic acid, and about 10% to about 20% vinyl lactam, by dry weight of solids, preferably about 80% to about 90% of a mixture of at least two alkyl acrylate or methacrylate esters, about 2% to about 5% ethylenically unsaturated carboxylic acid, and about 10% to about 20% vinyl lactam, by dry weight of solids. This water resistant adhesive for bandage is very effective in attaching to the skin of the user; but is difficult to peel without undue pain.

U.S. Pat. No. 6,077,589 to De Carvalho discloses adhesive tape. The adhesive tape substratum is embossed to provide an increased apparent thickness with protuberances and projections. The adhesive contacts the skin only at the apexes or extreme points of projections, leaving the remainder of the skin substratum distant. This arrangement allows free circulation of air and water vapor near to or around the non-adhered regions. The adhesive is said to be easier to peel, due to its limited contact area with the skin; but does not allow secure retention of the bandage.

U.S. Pat. No. 6,368,687 to Joseph et al. discloses a low trauma adhesive article. A low trauma pressure-sensitive adhesive coated substrate comprising a sheet material, tape or laminate structure designed to adhere to skin or like surfaces. The pressure-sensitive adhesive layer of this adhesive coated substrate is a fibrous adhesive layer generally having a basis weight of from 5 to 200 g/m$^2$ applied to a conformable backing or substrate. The fibrous adhesive layer has a textured outer face and persistent porosity between discrete adhesive fibers. Generally, the fibrous adhesive layer has a MVTR (measured by ASTM E 96-80 at 40° C.) of at least 1000 g/m²/day, preferably at least 6000 g/m²/day. The adhesive fibers comprise polyalphaolefin adhesive or acrylate pressure-sensitive adhesive. These fibers have to be bonded to the backing by means other than relying on the pressure sensitive adhesive coating applied to the fibers. The easy peel of these fibers is only due to the limited contact between the fibers and the skin surface. This limited skin contact feature also limits the adhesive property of the backing strip to the skin, preventing secure attachment of the bandage.

U.S. Pat. No. 6,566,577 to Addison et al. discloses wound dressings having low adherency. The wound dressings are of the island type, having as adhesive-coated backing sheet and an absorbent island supported on the backing sheet. The island comprises a layer of liquid absorbent material enclosed in an envelope of textured perforated ethyl methyl acrylate thermoplastic film. The film presents a ribbed or embossed perforated surface having low adherency to the wound. The film island at the rear surface of the envelope is perforated and smoothed to provide good attachment to the backing sheet with controlled water vapor transmission rate. The liquid absorbing island of the wound dressing has low adherency to the wound due to the presence of rib textured perforated thermoplastic film. The backing sheet that carries the absorbing island is adhered to skin to retain the wound dressing and no disclosure is provided for easily peeling this backing sheet from the skin with undue pain.

U.S. Pat. No. 6,743,964 to Yoshida et al. discloses a pad and adhesive bandage. A pad has an approximate-quadrangular portion and approximate-arched portions attached to both lateral sides of the approximate-quadrangular portion. All the periphery of the pad is sealed with ultrasonic treatment. L represents the length of the approximate-quadrangular portion in the direction parallel to the lateral axis, S represents the length of the approximate-quadrangular portion in the direction parallel to the vertical axis and R represents a radius of said approximate-arched portion. The geometrical relation between L, S and R satisfies following relations.

0.5S<or =L<or =4S between L and S;

0.5S<or =R<S between S and R.

The pad prevents peeling-off from four corners thereof and intrusion of water. This is a geometrical relationship between the dimensions of the elements of the adhesive pad when exposed to moisture. This disclosure does not suggest a method or means for enabling a bandage to be peeled easily without pain.

U.S. Pat. No. 6,747,183 to Siegwart et al. discloses an adhesive bandage with improved comfort and fit. An adhesive bandage having a backing material; an adhesive applied to at least one second major surface of the backing material; and a wound contacting a pad secured to the backing by a portion of the adhesive. The bandage has a tapered portion and a non-tapered portion with rounded edges. The length of the tapered portion of the bandage ranges from about 30% to about 70% of the total length of the bandage. The adhesive to bond the wound-contacting pad includes a hot melt adhesive or styrenic block copolymers and tackifying resins, or ethylene copolymers, including ethylene vinyl acetate copolymers. The adhesive for the bandage portion includes acrylic based, dextrin based, and urethane based adhesives as well as those based on natural rubber or synthetic elastomers including amorphous polyolefins, for example, amorphous polypropylene. The comfort of the adhesive bandage is due to the geometrical shape of the adhesive ends and does not allow easy painless removal of the bandage.

U.S. Pat. No. 6,942,683 to Dunshee discloses a wound closure system and method. The system uses a flowable adhesive together with wound closure such as wound bridge. The skin paint includes 1-40% of a siloxane-containing polymer; 60-99% of an Alkane-Based Siloxane Polymer Reaction Solvent; and 0-15% of adjuvants.

U.S. Pat. No. 6,946,177 to Abe et al. discloses an adhesive composition and adhered structure, which can be thermally peeled with ease. The adhesive composition contains (i) from 55 to 95 wt. % of a tackifying polymer and (ii) from 4 to 40 wt. % of a crystalline polycaprolactone polymer based on a total weight of the composition. The tackifying polymer is cross-linked polymer that is compatible with the polycaprolactone which melts upon application of heat allowing easy peel of the adhesive. Application of heat also heats the wound in addition to heating the adhesive ends of a bandage, which is extremely painful and damaging to the wound. After peeling, the melted polycaprolactone is retained on the skin, which may cause irritation of skin.

Notwithstanding the efforts of prior art workers to construct a bandage that adheres to the skin securely in wet and dry conditions, these progressive developments have inherently resulted in bandages that are more difficult to peel of the skin especially when the user of the bandage has hair on the skin, resulting in extreme pain. Compositions and structures that decrease adhesion due to the incorporation of monomeric precursors of polymers or the geometrical approaches that limit the area of contact of the adhesive with the skin also compromise the overall adhesion of the bandage, resulting in inferior products. There remains a need in the art for a flexible bandage that adheres well to the skin and is easily removable from the skin at will without causing excessive pain to the user. This need has been exacerbated by the inherent difficulty in creating an bandage adhesive that bonds well and, at the same time, can be readily removed with minimal pain during peeling of the bandage away from the skin.

SUMMARY OF THE INVENTION

The present invention provides a flexible bandage that adheres well to the skin and is readily removed upon demand. Bonding of the bandage to the skin is so strong that the bandage can remain securely in place—even under water—for an extended period of time. Removal of the bandage is painless. The user experiences substantially no pain during peeling of the bandage away from the skin.

Generally stated, the bandage has an adhesive layer comprising at least one pocket (and preferably a plurality of pockets) or a plurality of microcapsules of an adhesive inactivating ingredient that is readily released when the user desires to remove the bandage. The bandage for example, may be removed by the application of pressure to the external surface of the adhesive portion or by scratching the external surface of the bandage. This application of pressure causes the pockets or microcapsules to break, releasing the adhesive inactivating ingredient. Due to the arrangement of the microcapsules within the adhesive layer, the adhesive inactivating ingredient is released at the interface between the skin and the adhesive-coated backing layer, enabling the bandage to be peeled away from the skin easily and without pain.

The backing layer of the bandage may be provided with pockets that contain the adhesive inactivating ingredient. Alternatively, the adhesive inactivating ingredient may be contained in capsules or microcapsules that are applied concurrently with the adhesive layer of the bandage. The overall volume of the pockets or microcapsules determines the amount of the adhesive inactivating ingredient available.

Once released, the adhesive inactivating agents spread to an area at the skin-adhesive interface that defines the region of adhesive inactivation. The pockets included in the backing layer may be spaced apart, and the size of the pockets may be large enough to inactivate the adhesive in the region therebetween. However, when microcapsules are used, they may be distributed more uniformly and closely spaced, since each of the microcapsules contains only a small amount of the adhesive inactivating ingredient.

The adhesive inactivating ingredient is contained in pockets within the backing sheet in the first embodiment of the invention. In the second embodiment of the invention, the adhesive inactivating ingredient is contained in microcapsules that are incorporated in the adhesive layer. In the first embodiment, the backing sheet is fabricated from two polymeric sheets. The first polymeric sheet is embossed to create the packets and filled with the adhesive inactivating ingredient. The shape of the pockets may be spherical, cylindrical or elongated or any suitable shape. The pockets may be interconnected to form a continuous single pocket such as an interconnected channel. The pockets may be arranged to have a decorative shape such as a picture frame that is within a short, approximately 1/8 inch to 5/16 of an inch, distance from the edges of the bandage skin contacting portion. The central portion of the picture frame may have one or more x-shaped interconnected pockets providing a decorative appearance. The second polymeric sheet, which is substantially thinner, is bonded to the first sheet with embossed and ingredient filled pockets thereby encapsulating the adhesive inactivating ingredient in the backing sheet. The application of pressure or scratching the outer surface of the backing sheet breaks the pockets on the thinner second polymeric sheet thereby releasing the adhesive inactivating ingredient at the skin-adhesive interface.

The glue used for attachment to skin comprises acrylic based, dextrin based, and urethane based adhesives as well as those based on natural and synthetic elastomers. The adhesives may also include amorphous polyolefins including amorphous polypropylene, such as HL-1308 from HB Fuller or Rextac RT 2373 from Huntsman (Odesssa, Tex.). Water resistant adhesives include polymerization reaction product two alkyl acrylate or methacrylate ester monomers such as butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate with ethylenically unsaturated carboxylic acid, a vinyl lactam, and including a crosslinking agent.

It has been surprisingly found that an oily composition inactivates the adhesive. The oily composition comprises oils selected from vegetable oils such as olive oil, safflower oil, cotton seed oil, peanut oil, soybean oil, caster oil, sesame oil and the like and mineral based oils such as mineral oil or liquid paraffin. Other oily compositions include fatty acids that have a melting point lower than 20° C.

The oily adhesive inactivating ingredient may be contained in pockets of the embossed backing layer. The spreadability of the oily adhesive inactivating ingredient is determined by its volume, viscosity and its surface tension. Since pockets contain larger volume of the adhesive inactivating ingredient, they can be spaced apart further based on the volume. The volume is generally in the range of 0.01 cc to 0.5 cc and the spacing between the pockets is in the range of 0.01 cm to 0.2 cm. Microcapsules are generally small and contain only a small quantity of adhesive inactivating ingredient and can only spread over a small distance approximating a few times the diameter of the microcapsule. However, these microcapsules are added to the adhesive and are nearly uniformly dispersed in the adhesive layer. Therefore, the appropriate measure is the relative volume of the adhesive inactivating ingredient as compared to the volume of the adhesive. This ratio is typically in the ratio of 5 to 20%.

BRIEF DESCRIPTION OF THE DRAWING

The invention will be more fully understood and further advantages will become apparent when reference is had to the following detailed description of the preferred embodiments of the invention and the accompanying drawings, in which.

DETAILED DESCRIPTION OF THE INVENTION

Figure 1A:
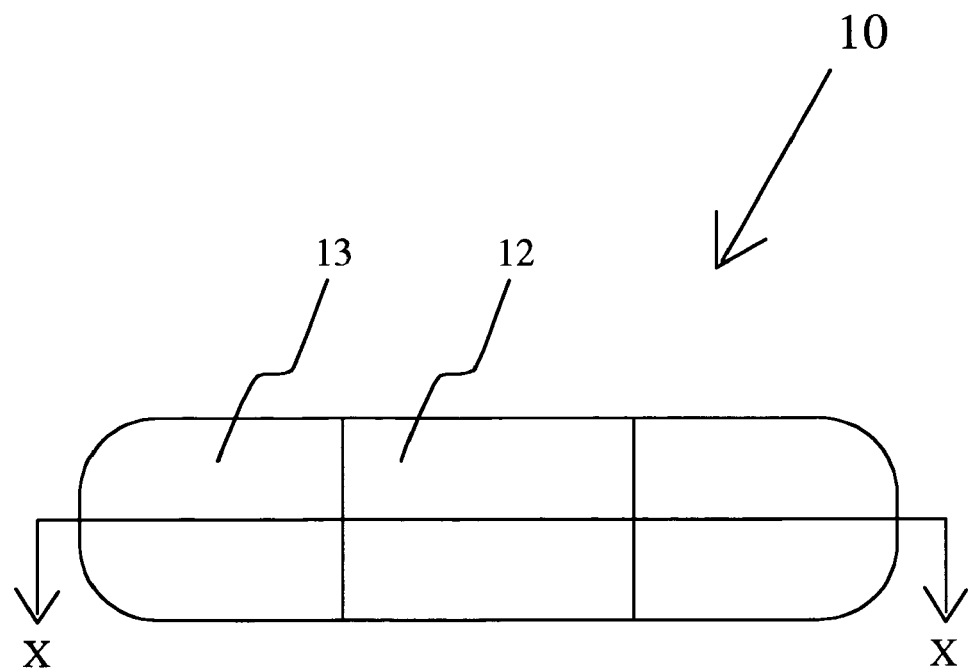
FIG. 1a is a schematic diagram of a front view of a conventional bandage with a wound contacting central pad and adhesive coated end tabs that attach to the skin.

The present invention provides bandage that is well bonded to the skin, and retains an absorbent pad, splint or the like, providing a secure medical retaining device. Notwithstanding its strong bond with the skin, the bandage can be readily peeled therefrom with virtually no pain at any time at the convenience of the wearer by either scratching or applying pressure to the outer surface of the backing layer of the bandage at the adhesive portion. This scratching action or application of pressure breaks pockets or microcapsules that release an adhesive inactivating ingredient at the skin-adhesive interface.

The bandage typically comprises a backing layer with a central region for attachment to an absorbent pad and two end portions which carry an adhesive coating that contacts the skin of the user and attaches the bandage. The absorbent pad that contacts the wound surface is attached to the central portion of the backing layer by hot melt glue or conventional strong glue. Examples of suitable adhesives include those based on styrenic block copolymers and tackifying resins such as HL-1491 from HB-Fuller Co. (St. Paul Minn.), H-2543 from ATO-Findley (Wawatausa, Wis.), and 34-5534 from National Starch & Chemical (Bridgewater, N.J.). Ethylene copolymers, including ethylene vinyl acetate copolymers, may also be used as adhesives to bond the absorbent pad to the backing sheet. This adhesive retains the absorbent pad on the backing strip and has nothing to do with peeling of the bandage from the skin. Bandages, which retain a splint or are used for sports purposes do not generally, contain this absorbent pad attached to the central portion of the backing layer.

The end portions of the backing layer are coated with an adhesive coating that permits the attachment of the bandage to the skin. There are specific requirements for the adhesive coating composition. First, it must be able to contact the skin for a prolonged period of time without irritating the skin. The adhesive must have sufficient strength to retain the bandage against the skin securely, thereby holding the absorbent pad in contact with the wound, or retaining a splint. The adhesive cannot be rigid and must be flexible enough to allow movement of the skin. Brittle adhesives crack and fail easily. Technical improvements in this area have focused on improving the quality of the adhesive and strengthening its bond to the skin. The adhesive must also exhibit a balance between its shear properties and adhesion properties, which are inversely related. In a "wet flex" performance test for adhesive bandages, when applied to fingers, the failure modes are: (i) "flagging", that is, when the overlapped bandage pops open due to a failure to adhere to itself; and (ii) "ring off", which occurs when the overlapped bandage loses adhesion to the skin and slips off. Typically, very soft, highly tacky adhesives exhibit low shear strength, while hard adhesives are only slightly tacky and exhibit high shear strength. An adequate degree of adhesive and shear properties are required so that no adhesive residue remains when the bandage is removed from the skin of the wearer.

The glue used for attachment of the bandage to the skin comprises acrylic based, dextrin based, and urethane based adhesives as well as those based on natural and synthetic elastomers. The adhesives may also include amorphous polyolefins including amorphous polypropylene, such as HL-1308 from HB Fuller or Rextac RT 2373 from Huntsman (Odesssa, Tex.). Water resistant adhesives include the polymerization reaction product of (i) two alkyl acrylate or methacrylate ester monomers such as butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, and methyl methacrylate with (ii) ethylenically unsaturated carboxylic acid, (iii) a vinyl lactam, and (iv) a crosslinking agent. Improvement in adhesive strength properties have resulted in adhesives that bond well to the skin and do not peel off or fall off even when the bandage becomes wet. Unfortunately, the same factors that improve the adhesive properties of a bandage, also make it very difficult to remove the bandage from the skin. This is especially the case when hair is present on the skin. Removal of a bandage that is highly adhesive tends to pull or dislodge the hair follicles from the skin, creating a very painful experience.

Prior art workers have contoured the shape of the adhesive portion of the bandage to prevent edge peel. Efforts have been made to incorporate monomeric acrylates or polyols to weaken the adhesive, or to utilize additives that degrade the adhesive as a function of time. These approaches deteriorate the adhesive, reducing its performance. Prior art workers have also attempted to emboss the backing layer, thereby limiting the contact regions of the adhesive with the skin. This approach limits the adhesive contact, thereby reducing the bonding strength of the bandage.

It has been surprisingly found that an oily composition inactivates the adhesive. The oily composition comprises one or more oils selected from a vegetable source such as olive oil, safflower oil, cotton seed oil, peanut oil, soybean oil, caster oil, sesame oil and the like and mineral based oils such as mineral oil or liquid paraffin. Other oily compositions include fatty acids that have a melting point lower than 20° C.

The first embodiment of the invention uses pockets that encapsulate the adhesive inactivating ingredient in the backing layer of the bandage. This is conveniently accomplished by preparing the backing layer as a two polymeric sheet construction, wherein the first polymeric sheet is embossed to create pockets. These embossing shapes may be spherical, cylindrical or elongated and may be individually separated or interconnected. The pockets are filled with an adhesive inactivating ingredient. A second polymeric sheet, which is generally thinner and has low strength properties, is spread over the first polymeric sheet, covering the pockets. It is then heat sealed or sealed by other methods to encapsulate the adhesive inactivating ingredient. This backing layer is processed in the usual way by attaching the absorbent pad using hot melt glue and applying the skin contacting adhesive to the end portions of the bandage. When pressure is applied to the outer surface of the backing layer, or the backing layer is scratched, the pockets at the second polymeric sheet rupture, releasing the adhesive inactivating ingredient at the skin-adhesive interface. This release provides for easy, pain free removal of the bandage, and can be triggered at any time that suits the convenience of the wearer.

The second embodiment uses a standard backing layer commonly used to fabricate bandages. The absorbent pad is attached at a central location by hot melt glue. The adhesive that is applied to the skin contacting end portions of the backing layer includes microcapsules that contain the adhesive inactivating ingredient. The adhesive bonds to the skin effectively and the bandage is retained on the skin in the usual manner. When release the bandage is desired, the wearer applies pressure to the adhesive portion of the bandage, or scratches this region. The microcapsules rupture, releasing the adhesive inactivating ingredient at the skin-adhesive interface. With this release, there is effected a pain-free, effortless removal of the bandage.

When a pocket or microcapsule breaks, it releases the adhesive inactivating ingredient. How far the ingredient spreads is a function of the volume of ingredient contained in the pocket or microcapsule, and its viscosity and surface tension, or wetting characteristics. High viscosity oils spread slowly. Reduced surface tension promotes spreadability. Surfactants reduce the surface tension and improve spreading capability. Viscosity may be increased by the addition of thickeners. The pockets are generally larger and therefore contain a larger volume of the adhesive inactivating ingredient, and can spread the ingredient over a larger distance. Typically the pockets may have a volume of 0.01 cc to 0.5 cc and the spacing between the embossed pockets in the backing layer may be 0.01 cm to 0.2 cm.

The microcapsules are generally small in diameter and contain only a small volume of the adhesive inactivating ingredient. The adhesive inactivating ingredient spreads approximately a few times the diameter of the microcapsule. However, there are many microcapsules, nearly uniformly distributed in the adhesive layer. The appropriate measure of adhesive inactivating ingredient is its overall volume as compared to the volume of the adhesive used. The adhesive inactivating ingredient volume is typically present in the range of about 5 to 20% of the volume of the adhesive used. In this manner, the adhesive contains the microcapsules, with the adhesive inactivating ingredient nearly uniformly distributed, and affords sufficient volumetric release of the adhesive inactivating ingredient for effective bandage removal.

The oily composition should be contained in the pockets or microcapsules indefinitely without chemical reaction or dissolution. The second polymeric sheet encasing the pockets may include a layer of polyethylene, which is immune to dissolution by oily compositions. The adhesive inactivating ingredient may be contained in microcapsules of polymeric or gelatin composition. Use of gelatin, which dissolves in water, is not a problem when the adhesive used is water resistant.

The method of manufacture of the microcapsules is well known in the art and includes formation of polymeric bubbles that contain the adhesive inactivating ingredient. For example, soybean oil can be easily micro encapsulated in the reaction product of ethylene diamine and toluene diisocyanate. Techniques for producing microcapsules are detailed in 'Microcapsules and other capsules-Advances since 1975', edited by M. H. Gutcho, 1979 published by Noyes Data Corporation, the disclosure of which is specifically incorporated herein by reference.

FIG. 1a shows generally at 10 a schematic diagram of a front view of a conventional bandage with a wound-contacting central pad 12 and adhesive coated end tabs 13 that attach the bandage to the skin.

Figure 1B:
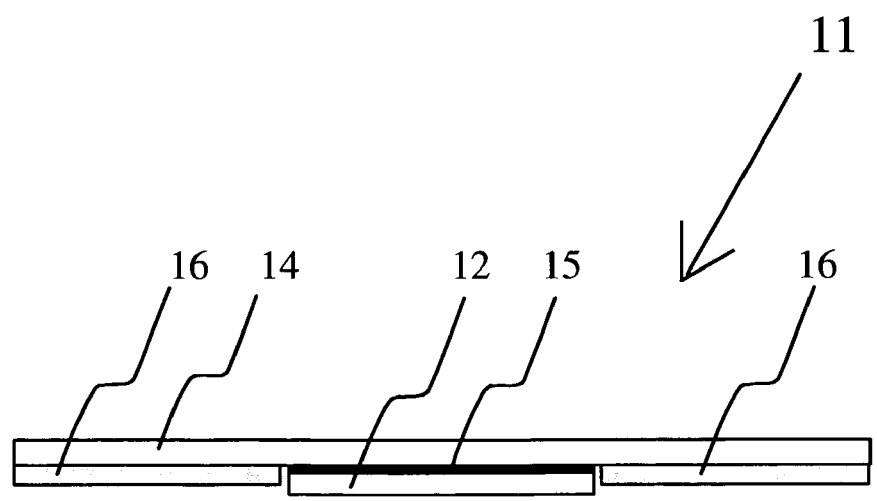
FIG. 1b is a schematic diagram of a cross sectional view of a conventional bandage showing a wound contacting central pad, its attachment to a backing layer and an adhesive coating provided on the backing layer in the end tabs for attachment to the skin.

FIG. 1b shows generally at 11 a schematic diagram of the cross section of a conventional bandage, taken along the line XX of FIG. 1a. The wound contacting central pad 12 is bonded to the backing layer 14 with hot melt or other permanent adhesive 15. The backing layer is coated with a skin contacting adhesive 16 on end tabs.

Figure 2A:
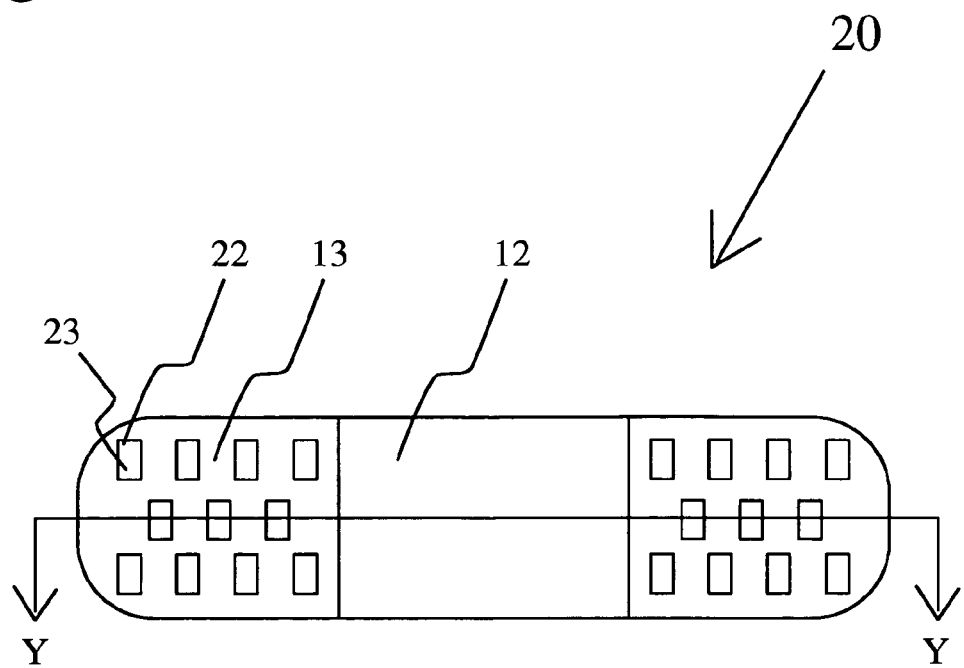
FIG. 2a is a schematic diagram of the first embodiment of the invention depicting the front view of the bandage with pockets of adhesive inactivating ingredient contained within the backing layer of the adhesive coated end tabs of the bandage.

FIG. 2a shows generally at 20 a schematic diagram of the first embodiment of the invention depicting the front view of a bandage with a wound contacting central pad 12 and adhesive coated end tabs 13 that attach the bandage to the skin. The end tabs 13 have a plurality of pockets 22 which contain an adhesive inactivating ingredient 23. The pockets will be covered by the adhesive on the skin contacting side. They will be buried within the backing layer and will not be visible. Pockets 22 are shown in the drawing for clarity.

Figure 2B:
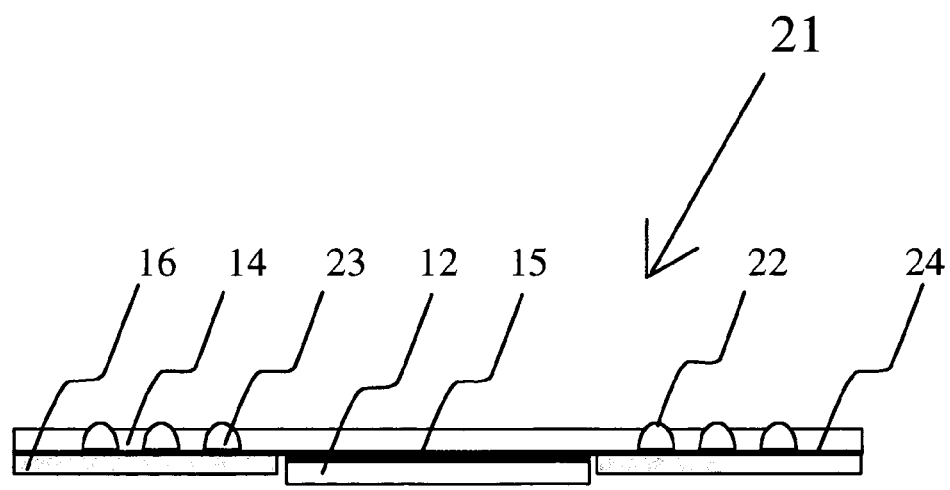
FIG. 2b is a schematic diagram of a cross sectional view of a bandage according to the first embodiment of the invention showing wound contacting central pad, its attachment to a backing layer, a backing layer with pockets that contain an adhesive inactivating ingredient and the adhesive coating provided on the backing layer in the end tabs for attachment to the skin.

FIG. 2b shows generally at 21 a schematic diagram of the cross section of a bandage of the first embodiment of the present invention, taken along the line YY of FIG. 2a. The wound contacting central pad 12 is bonded to the backing layer 14 with hot melt or other permanent adhesive 15. The backing layer 14 contains pockets 22, which contain adhesive inactivating ingredient 23. The backing layer 14 is sealed with a second polymeric sheet 24. The adhesive layer 16 coats the second polymeric sheet 24.

Figure 3A:
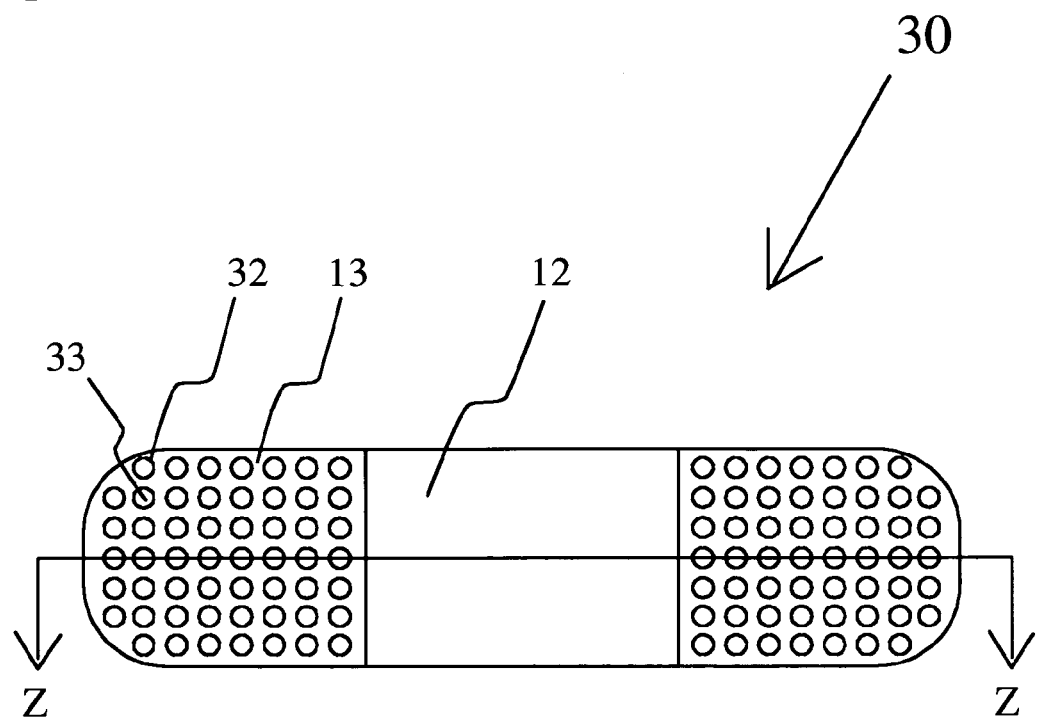
FIG. 3a is a schematic diagram of the second embodiment of the invention depicting the front view of the bandage with an adhesive inactivating ingredient contained in the form of microcapsules that are present within the adhesive layer of the end tabs of the bandage.

FIG. 3a shows at 30 a schematic diagram of the second embodiment of the invention illustrating the front view of a bandage with wound contacting central pad 12 and adhesive coated end tabs 13 that attach the bandage to the skin. The adhesive contains a plurality of microcapsules 32 that contain the adhesive inactivating ingredient 33 within the adhesive layer of the bandage's adhesive coated end tabs 13. The microcapsules will be generally invisible, since they are contained within the adhesive coating of the end tabs. They are shown for clarity.

Figure 3B:
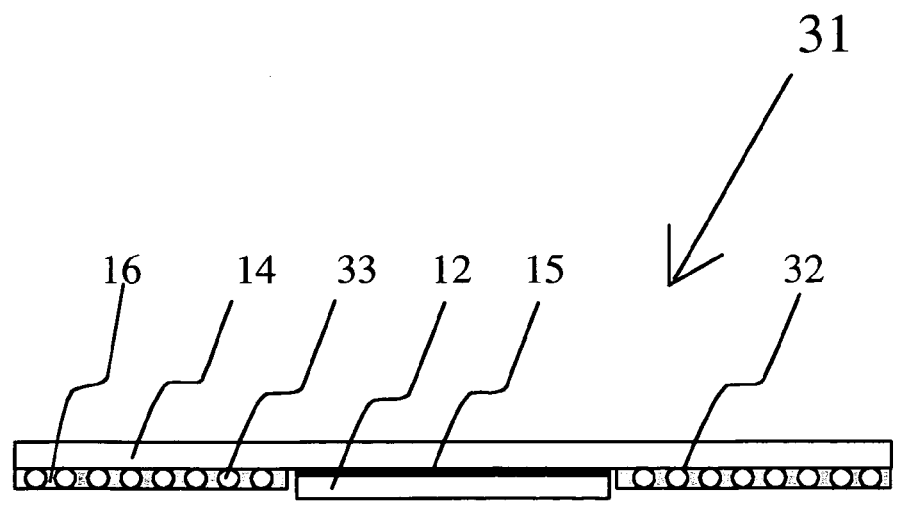
FIG. 3b is a schematic diagram of a cross sectional view of a bandage according to the second embodiment of the invention showing a wound contacting central pad, its attachment to a backing layer, and end tabs with an adhesive coating on the backing layer which contains a plurality of microcapsules that encapsulate adhesive inactivating.

FIG. 3b shows at 31 a schematic diagram of the cross section of a bandage according to the second embodiment of the invention, taken along line ZZ of FIG. 3a. The wound-contacting central pad 12 is bonded to the backing layer 14 with hot melt or other permanent adhesive 15. The backing layer 14 has a coating of adhesive 16 in the skin contacting areas of the bandage, which contains microcapsules 32 with adhesive inactivating ingredient 33.

The key features of the easy to peel securely attaching bandage includes, in combination, the features set forth below:

1. a bandage having a backing layer;
2. the backing layer having a plurality of portions coated with adhesive for attachment to skin;
3. optionally the backing layer having a central portion permanently attached to an absorbent pad;
4. the backing layer comprising individually separated or interconnected pockets of an adhesive inactivating ingredient or the adhesive-containing microcapsules of an adhesive inactivating ingredient;
5. application of pressure to or scratching the outer surface of the backing layer being operative to break the pockets or microcapsules, thereby releasing the adhesive inactivated ingredient at the skin-adhesive interface; and
6. the adhesive inactivating ingredient being an oil selected from the group consisting of vegetable oils such as olive oil, safflower oil, cotton seed oil, peanut oil, soybean oil, caster oil, sesame oil, mineral based oils such as mineral oil or liquid paraffin or fatty acids, and mixtures thereof.

The easy to peel securely attaching bandage disclosed herein can be modified in numerous ways without departing from the scope of the invention. For example, different bandages geometries, diverse dispersions of adhesive inactivating ingredient compartments, and a variety of release methods may be used. These and other modifications are intended to fall within the scope of the invention, as defined by the subjoined claims.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A bandage, comprising:
   a. a backing layer;
   b. a plurality of portions of the backing layer containing an adhesive appointed for contact with skin of a bandage wearer;
   c. a plurality of pockets containing an adhesive-inactivating ingredient disposed in the adhesive-containing portions of the backing layer;
   d. said pockets being operative to rupture upon application of pressure or scratching by the bandage wearer, thereby releasing said adhesive-inactivating ingredient;
   e. said adhesive-inactivating ingredient, upon release, being delivered at the skin contacting interface of said adhesive, reducing adhesive bond strength and enabling pain-free removal of said bandage;
   f. a central wound-contacting absorbent pad bonded by hot melt glue or strong adhesive to said backing layer; and
   g. wherein said backing layer is embossed with pockets, filled with said adhesive-inactivating ingredient and sealed with a second polymeric layer prior to the application of said adhesive.

2. A bandage as recited by claim 1, wherein the adhesive is selected from a group consisting of acrylic based, dextrin based, and urethane based adhesives, and adhesives based on natural and synthetic elastomers.

3. A bandage as recited by claim 1, wherein the adhesive releasing ingredient is a member selected from the group consisting of vegetable oil, olive oil, safflower oil, cotton seed oil, peanut oil, soybean oil, caster oil, sesame oil, mineral oil, liquid paraffin or fatty acids, and mixtures thereof.

4. A bandage as recited by claim 1, wherein said pockets have a volume ranging from about 0.01 cc to 0.5 cc and are spaced apart by a distance ranging from about 0.01 cm to 0.2 cm.

5. A method for producing an easy-to-peel, securely attaching bandage, comprising the steps of:
   a. selecting a first polymeric layer;
   b. embossing said first polymeric layer to form a plurality of pockets therein;
   c. filling said pockets with an adhesive-inactivating ingredient;
   d. selecting a second polymeric layer;
   e. spreading said second polymeric layer over said first polymeric layer to cover said filled pockets;
   f. bonding said second polymeric layer to said first polymeric layer to form filled pockets of adhesive-inactivating ingredient having a backing layer; and
   g. applying skin-contacting adhesive to portions of said backing layer, whereby release of the adhesive-inactivating ingredient can be triggered, and said bandage can be removed from the skin easily and without pain, when the wearer applies pressure to or scratches the backing layer, causing rupture of said pockets.

* * * * *